(12) United States Patent
Birngruber et al.

(10) Patent No.: US 6,234,633 B1
(45) Date of Patent: May 22, 2001

(54) METHOD FOR THE TOPOGRAPHIC DISPLAY OF FLUORESCENT INTERIOR SURFACES

(75) Inventors: Reginald Birngruber; Joachim Noack; Ursula Schmidt-Erfurth, all of Luebeck (DE)

(73) Assignee: Medizinisches Laserzentrum Luebeck GmbH, Luebeck (DE)

( * ) Notice: Subject to any disclaimer, the term of this patent is extended or adjusted under 35 U.S.C. 154(b) by 0 days.

(21) Appl. No.: 09/431,162

(22) Filed: Nov. 1, 1999

(30) Foreign Application Priority Data

Oct. 30, 1998 (DE) ............................................... 198 50 149

(51) Int. Cl.⁷ ......................................................... A61B 3/00
(52) U.S. Cl. ............................................................. 351/246
(58) Field of Search ................................... 351/205, 206, 351/221, 246; 356/317; 250/458.1, 459.1

(56) References Cited

U.S. PATENT DOCUMENTS 5,737,077 * 4/1998 Lee et al. ............................... 356/317

FOREIGN PATENT DOCUMENTS 44 27 101 A1   2/1996  (DE).

* cited by examiner

*Primary Examiner*—George Manuel
(74) *Attorney, Agent, or Firm*—Evenson, McKeown, Edwards & Lenahan, P.L.L.C.

(57) ABSTRACT

A method for the topographic display of interior surfaces of an object, for example, leakages on vessels of biological material by means of fluorescence angiography, in the case of which fluorescence images are produced in several planes of different depths and a fluorescent segmental chart is obtained therefrom.

21 Claims, 4 Drawing Sheets

METHOD FOR THE TOPOGRAPHIC DISPLAY OF FLUORESCENT INTERIOR SURFACES

BACKGROUND AND SUMMARY OF THE INVENTION

The present invention relates to a method for the topographic display of interior surfaces of an object, wherein the object is laterally scanned by means of a laser beam and fluorescence induced in the process is detected as a function of the site.

Topographic or site-resolved fluorescence display is used, for example, in the medical field for the fluorescent angiography of vessel display on a body organ. For this purpose, an exogenous fluorescent dye, such as fluorescein or indocyanine green, is injected into the patient's blood stream. The fluorescence of the dye is then excited by the punctiform scanning of the organ, for example, an eye, by means of a laser beam of a suitable wavelength and is detected by a detector in a laterally site-resolved manner. In the obtained fluorescent image, the vessel structures appear light before the darker background. Vessel leakages appear as regions of increased fluorescence. A conventional fluorescence display makes it possible to very precisely determine the site of the fluorescence in the lateral direction. However, no information is obtained concerning the depth of the fluorescence.

It is therefore an object of the present invention to provide a method of the above-mentioned type by means of which a three-dimensional fluorescence display is obtained.

This and other objects are achieved according to the present invention by fluorescent images being produced not only laterally but also at different depths (z-direction) confocally. For example, 32 fluorescence images in planes of different depths can be produced. As a result, a three-dimensional data matrix of fluorescence intensities is obtained. The number of matrix elements may in each case amount to, for example, 256 in the lateral direction (x and y) and 32 in the axial direction (z), corresponding to the different sectional planes. From this total data set of fluorescence intensities, the fluorescence depth profile $F_r(z)$ of the fluorescence intensity can be extracted as a function of the depth (z) for each lateral position.

The determination of the depth of the site at which the fluorescence occurs is carried out independently of the absolute amount of the fluorescence intensity. For this purpose, the course of the fluorescence depth profile is evaluated with respect to characteristics of the curve of the fluorescence depth profile. Such characteristics may, for example, be a turning point, certain sites of the monotonous curve ascent to the maximum of the curve, the maximum of the curve itself or the like. When analyzing the individual fluorescence depth profiles, the same characteristic of the course of the curve is always analyzed in order to determine the depth at which fluorescence "starts" In a preferred manner, a scaling of the fluorescence depth profile or of the curve of this profile is carried out so that the analysis becomes independent of the absolute value of the fluorescence intensity.

According to one aspect of the present invention, the depth at which fluorescence "starts" is defined at the site at which the fluorescence for the first time exceeds a certain fraction c, for example, 80% of the maximal value of the fluorescence depth profile. The determination of the depth for each lateral site, in which the fluorescence "starts", leads to a topographic chart of the fluorescence problem and thus to a confocally achieved topography of fluorescent interior surfaces in the object. This topography can, on the one hand, be coded in gray stages and can, on the other hand, be displayed as a perspective representation. In these displays, for example, in the case of the fluorescence angiography on the fundus of the eye, the retinal vessels can be recognized as clear elevations. As a result of the visualizing of the three-dimensional surface of the fluorescent structures, a basic expansion of the fluorescence display is obtained. For example, in fluorescence angiography, vascular changes can be diagnosed. In addition, the control of the course and the evaluation of therapeutic successes can be carried out in the case of vascular diseases. By means of displaying vessel leakages, a three-dimensional function image of the vessel structure is obtained. In addition, examinations of the skin can be carried out.

A preferred use of the invention takes place in examinations on the eye, particularly on the fundus of the eye.

BRIEF DESCRIPTION OF THE DRAWINGS

Other objects, advantages and novel features of the present invention will become apparent from the following detailed description of the invention when considered in conjunction with the accompanying drawings.

DETAILED DESCRIPTION OF THE DRAWINGS

Figure 1:
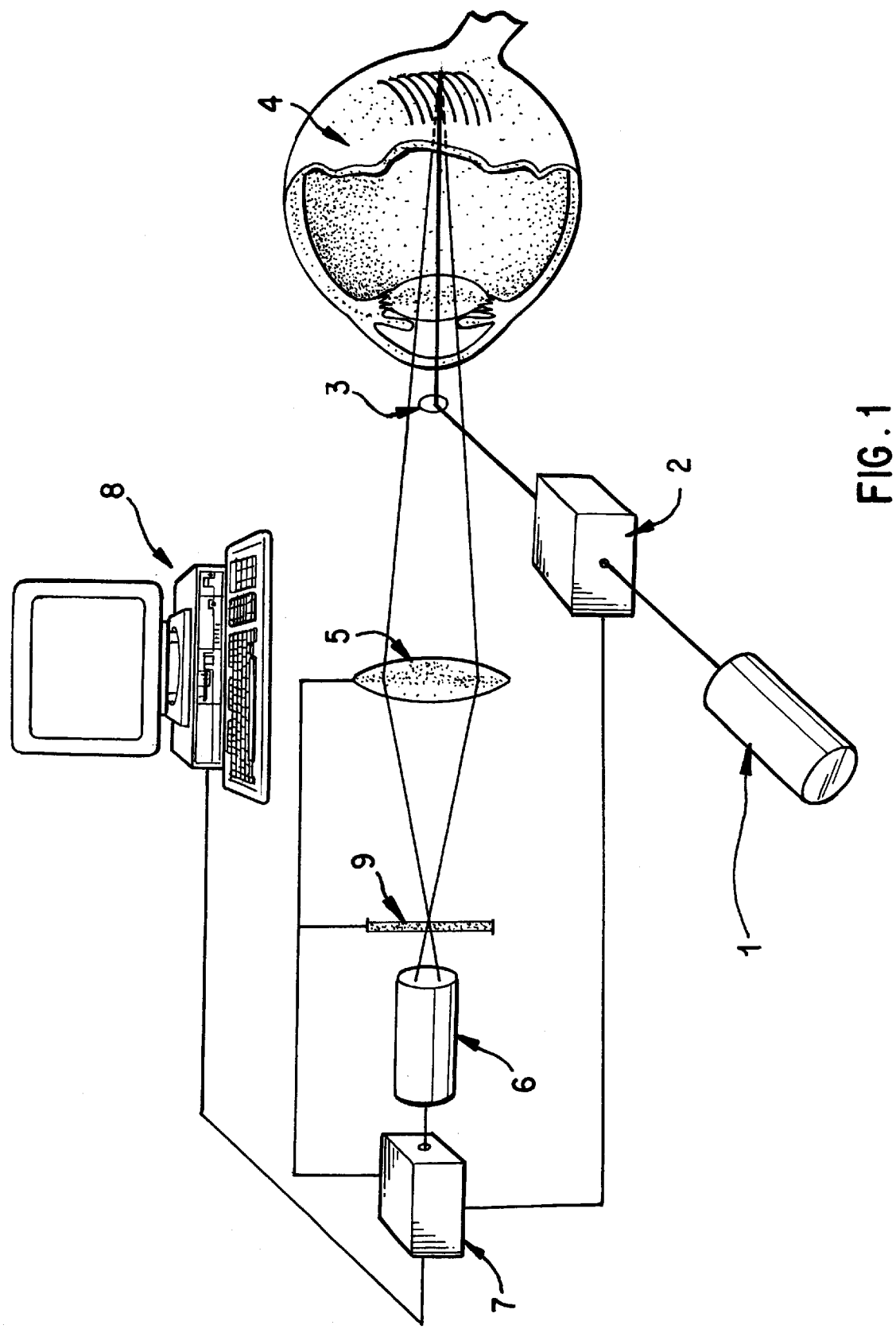
FIG. 1 is a schematic representation of the system by means of which the method of the invention can be carried out.

FIG. 1 illustrates one embodiment of the present invention, wherein a laser beam source 1 is aimed by a lateral (x,y)-deflection device 2 and a deviating device 3 onto the fundus of an eye 4. The fluorescence induced by this laser beam in the vessels of the fundus of the eye is detected by means of confocal ophthalmoscopy. For this purpose, a focusing device 5 is provided which, together with a confocal screen 9, as in the case of conventional confocal microscopy, guides the fluorescence intensities induced in different depths (z-direction) in respective sectional planes to a detector 6. As a result of displacement of, for example, the focusing lens system or of the confocal screen 9, the fluorescence intensities for respective sites of a three-dimensional data point grid 15 (FIG. 3) can be determined. In the two lateral directions (x, y), for example, 256 grid points respectively may be situated and, in the axial direction (z), 32 grid planes may be provided. An electronic system 7 is connected with the detector 6, through which detected fluorescence passing through the lateral (x, y) deflection device 2, the focusing lens system 5 and the confocal screen 9, can be assigned to respective sites of the data point grid 15 and can be stored in a memory 10 (FIG. 2) of an image processing device 8.

Figure 2:
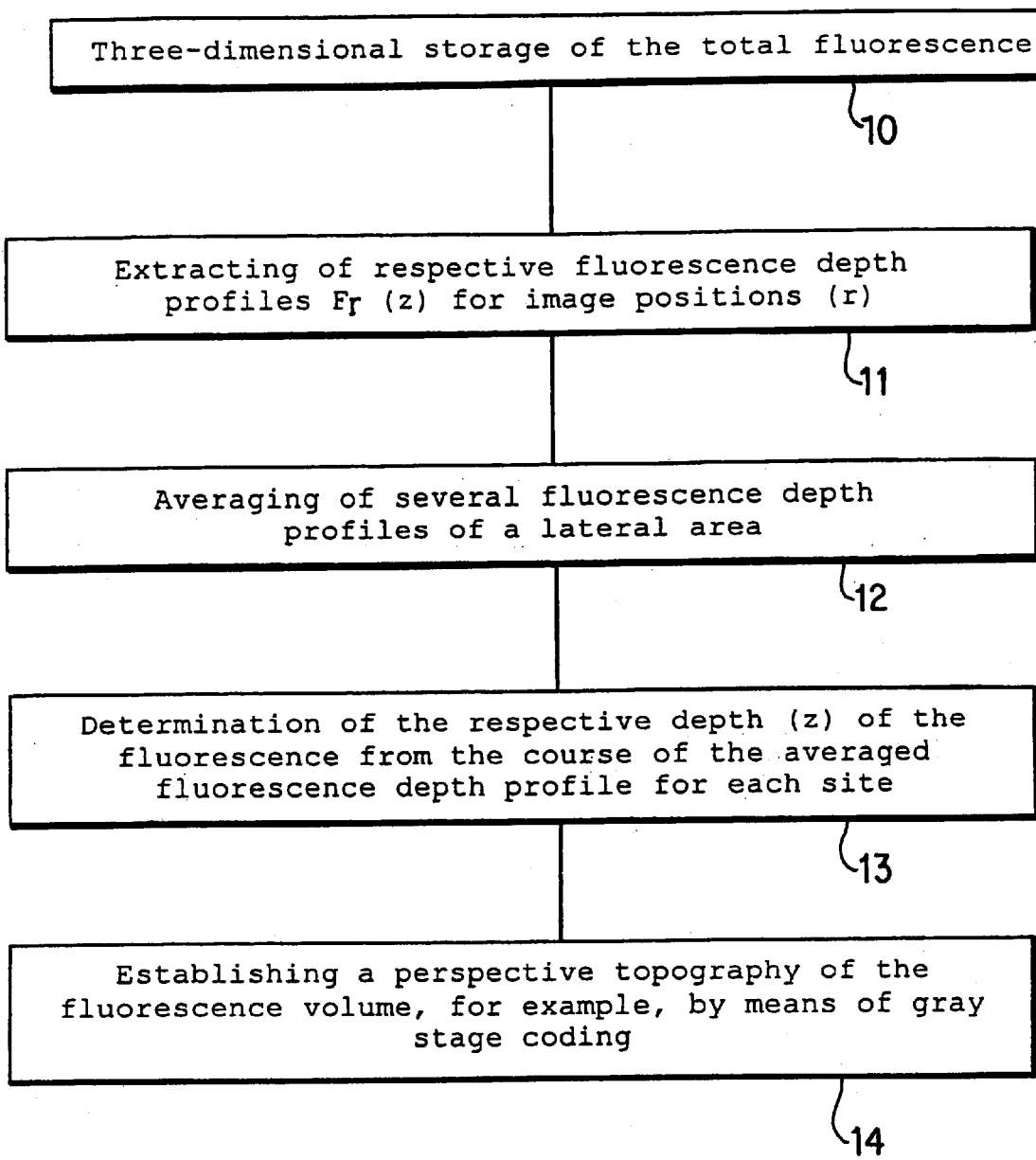
FIG. 2 is a chart describing the analyzing device of FIG. 1, which analyzing device carries out the storing of the obtained fluorescence intensity data and the processing of these data for preparing a three-dimensional image.
Figure 3:
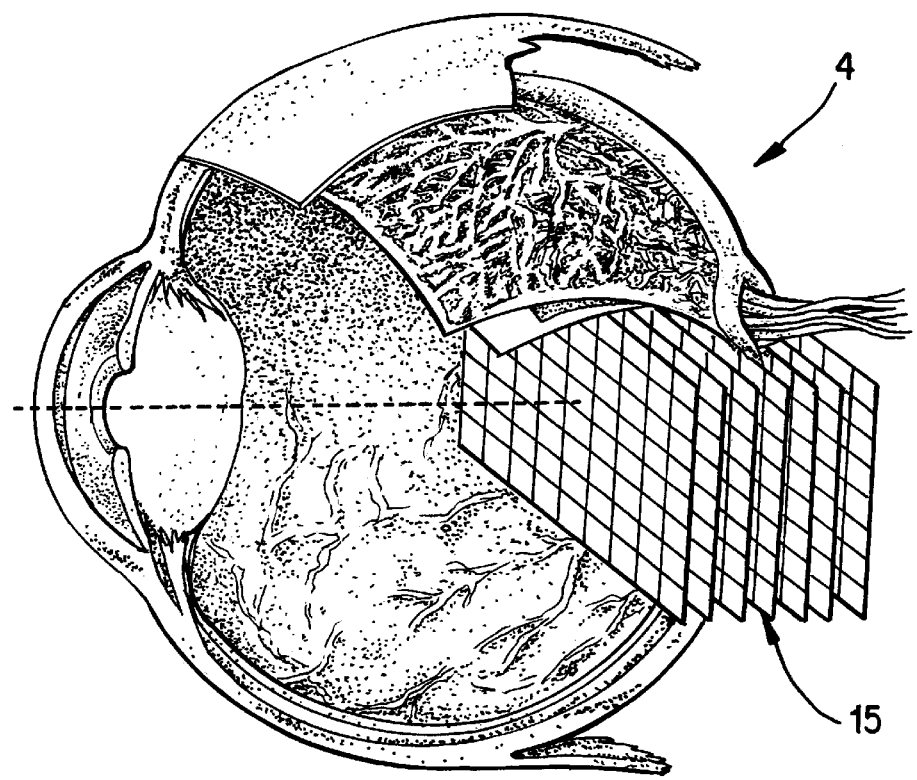
FIG. 3 is a representation of the different depths, from which fluorescence images are shown by means of the example of the fundus of an eye.
Figure 4:
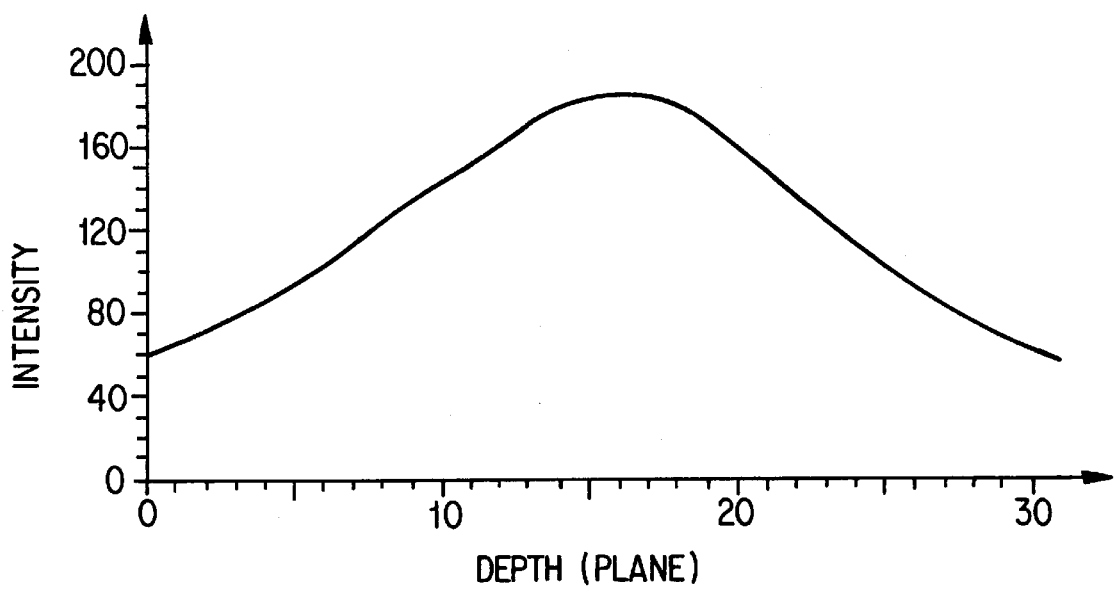
FIG. 4 is a view of a fluorescence depth profile produced, for example, by a lateral averaging.

From this three-dimensional total dataset of the fluorescence, for respective lateral positions (r), a fluorescence depth profile $F_r(Z)$ is extracted which indicates the fluorescence intensity as a function of the depth (z), as illustrated schematically by step 11 in FIG. 2. A clear noise may be superimposed on the course of the fluorescence depth profile. This may be electronic noise and not completely corrected movement artefacts on the basis of an object movement during the taking of the data point grid. In the case of many objects, particularly in biological tissue, it may be assumed that the fluorescence intensity within an image plane changes continuously and not abruptly. For reducing the influence of the noise on the fluorescence profile, a lateral averaging can be carried out over a certain range; for example, a lateral averaging over an environment with 7×7 lateral positions. This will then result in a clear reduction of the noise on the fluorescence depth profile. The averaging can take place in a step 12 of FIG. 2. FIG. 4 shows such a fluorescence depth profile obtained by lateral averaging and smoothing.

From the course of the curve of the respectively determined fluorescence depth profiles, which has preferably also been scaled (maximum=1), the depth (z) at which fluorescence starts can be determined (step 13 in FIG. 2). Because of the low depth resolution of the confocal method, even abrupt transitions, as, for example, on vessels, only cause a gradual rise of the fluorescence intensity with an increasing depth. The depth at which fluorescence "starts" is defined as the site at which, for the first time, the fluorescence exceeds a certain fraction (c), for example, 80% of the maximal value. Other characteristics in the course of the curve, such as a turning point or a certain gradient in a monotonous rise or the like can also be used for the analysis.

Figure 5:
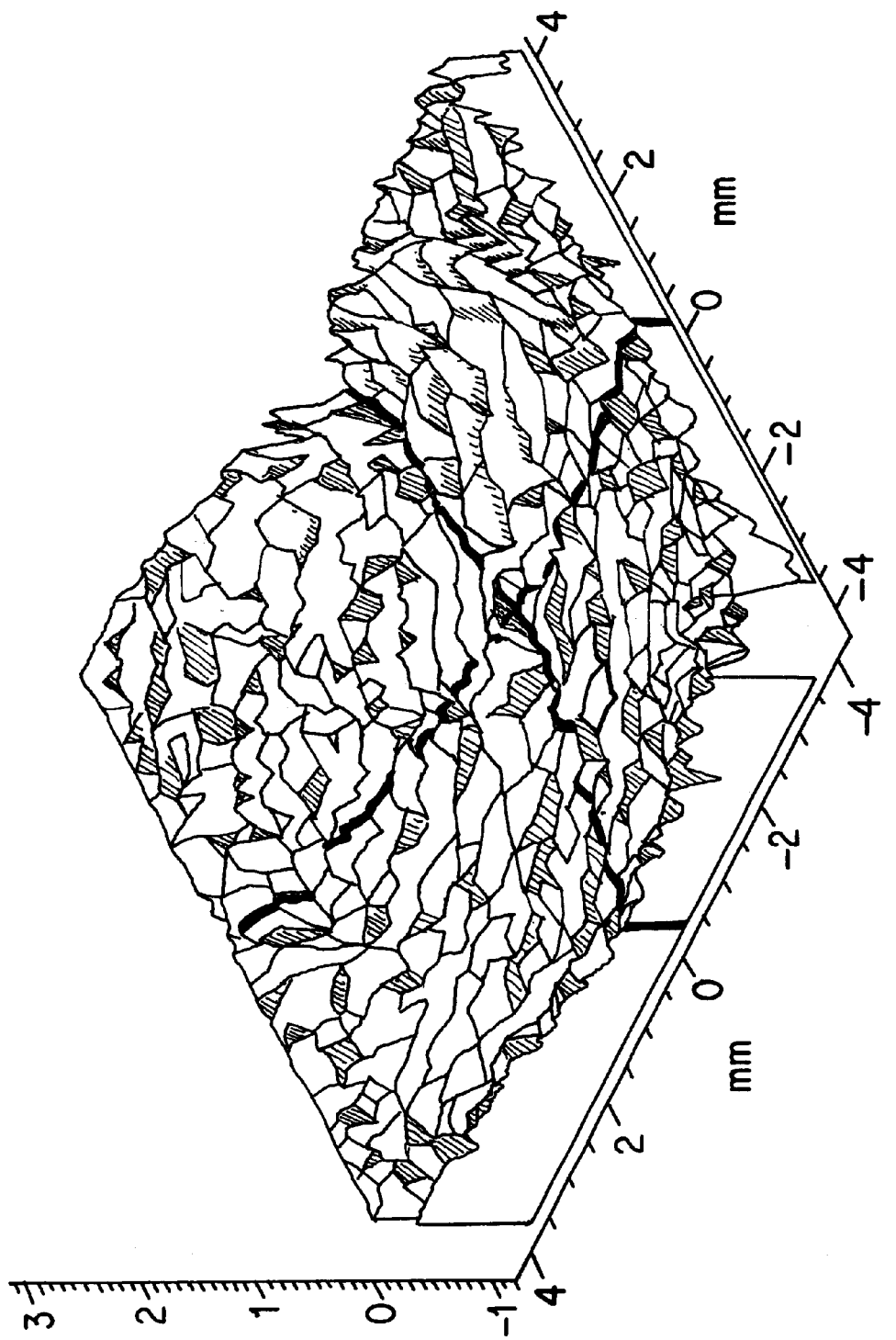
FIG. 5 is a perspective representation of a vessel topography on the fundus of the eye obtained by means of the invention.

The determination of the depth at which fluorescence "starts" for each site results in a topographic chart of the fluorescence volume which may, for example, be coded in gray stages or be displayed as a perspective representation. This takes place in step 14 of FIG. 2, the obtained topographic chart being shown as a perspective representation in FIG. 5. In this representation, for example, the retinal vessels of a fluorescence angiogram of the fundus of the eye can be recognized as clear elevations.

Since, for taking the 32 fluorescence images in the different depths, a certain time (approximately 1.5 to 2 seconds) is required, a movement of the object, for example, of the eyeball, may occur. In this case, the individual planes, in which the fluorescence images are situated, can first be aligned by means of characteristic features which compensates for eye movement. In this respect, rotational as well as translational movements can be taken into account. For the alignment of the individual sectional planes, one plane in an average depth range is selected as a reference plane and all other fluorescence images are aligned with respect to this reference plane. As a result, the accumulation of recording errors is avoided which may occur during the aligning of adjacent sectional images.

The foregoing disclosure has been set forth to illustrate the invention and is not intended to be limiting. Since modifications of the disclosed embodiments incorporating the substance of the invention may occur to persons skilled in the art, the invention should be construed to include everything within the scope of the appended claims and equivalents thereof.

We claim:

1. A method for topographically displaying interior surfaces of an object comprising:

laterally scanning the object with a laser beam to induce fluorescence in the object;

detecting induced fluorescence as a function of the scanned site;

confocally scanning the object at different depths;

determining a fluorescence depth profile for respective lateral image positions to indicate fluorescence intensity as a function of the depth; and determining a depth of a fluorescence site by analyzing a course of the fluorescence depth profile.

2. A method according to claim 1, further comprising generating the fluorescence by a fluorescence dye which is applied in the object.

3. A method according to claim 2, wherein the depth of the fluorescence site is determined by using a preselected characteristic of respective courses of curves of the fluorescence profiles.

4. A method according to claim 2, further comprising forming a lateral average of fluorescence depth profiles of several image positions of a lateral area for determining the depth of the fluorescence site.

5. A method according to claim 1, further comprising applying the fluorescence dye by injection or in a contact process in the object.

6. A method according to claim 5 wherein the depth of the fluorescence site is determined by using a preselected characteristic of respective courses of curves of the fluorescence profiles.

7. A method according to claim 5, further comprising forming a lateral average of fluorescence depth profiles of several image positions of a lateral area for determining the depth of the fluorescence site.

8. A method according to claim 1, further comprising generating the fluorescence by at least one fluorescence dye naturally present in the object.

9. A method according to claim 8, wherein the depth of the fluorescence site is determined by using a preselected characteristic of respective courses of curves of the fluorescence profiles.

10. A method according to claim 8, further comprising forming a lateral average of fluorescence depth profiles of several image positions of a lateral area for determining the depth of the fluorescence site.

11. A method according to claim 1, wherein the depth of the fluorescence site is determined by using a preselected characteristic of respective courses of curves of the fluorescence profiles.

12. A method according to claim 11, further comprising using a turning point, a maximum, a fraction of the maximum or a certain gradient of a monotonous curve portion as the characteristic.

13. A method according to claim 12, further comprising forming a lateral average of fluorescence depth profiles of several image positions of a lateral area for determining the depth of the fluorescence site.

14. A method according to claim 11, further comprising forming a lateral average of fluorescence depth profiles of several image positions of a lateral area for determining the depth of the fluorescence site.

15. A method according to claim 1, further comprising forming a lateral average of fluorescence depth profiles of several image positions of a lateral area for determining the depth of the fluorescence site.

16. A method according to claim 1, further comprising scaling the fluorescence depth profile.

17. A method according to claim 1, further comprising aligning planes in which fluorescence images are generated by determining one plane of an average depth as a reference plane and aligning the fluorescence images of remaining planes with respect to the reference plane.

18. A method according to claim 1, wherein the object is biological tissue.

19. A method according to claim 1, wherein the object is an eye.

20. A method according to claim 19, wherein the fundus of the eye is examined.

21. A method according to claim 1, wherein the object is skin.

* * * * *